United States Patent [19]

Frankel et al.

[11] Patent Number: 5,169,774
[45] Date of Patent: Dec. 8, 1992

[54] MONOCLONAL ANTI-HUMAN BREAST CANCER ANTIBODIES

[75] Inventors: Arthur E. Frankel, Durham, N.C.; David B. Ring, Redwood City; Walter Laird, Pinole, both of Calif.

[73] Assignee: Cetus Oncology Corporation, Emeryville, Calif.

[21] Appl. No.: 190,778

[22] Filed: May 6, 1988

Related U.S. Application Data

[63] Continuation of Ser. No. 842,476, Mar. 21, 1986, which is a continuation-in-part of Ser. No. 690,750, Jan. 11, 1985, Pat. No. 4,753,894, which is a continuation-in-part of Ser. No. 577,976, Feb. 8, 1984, abandoned.

[51] Int. Cl.$^5$ ............... C12N 5/12; C07K 15/14; G01N 33/574
[52] U.S. Cl. ............... 530/388.85; 436/548; 436/64; 436/813; 530/808; 530/864; 935/106; 935/110; 435/172.2; 435/7.23; 435/240.27
[58] Field of Search ............... 435/172.2, 240.27, 7.23; 436/548, 813; 530/387, 808, 388.8, 388.85, 387.5, 387.7; 935/106, 110

[56] References Cited

U.S. PATENT DOCUMENTS

| | | | |
|---|---|---|---|
| 4,172,124 | 10/1979 | Koprowski et al. | 424/85 |
| 4,340,535 | 7/1982 | Voisin et al. | 435/172.2 |
| 4,359,457 | 11/1982 | Neville, Jr. et al. | 435/172.2 |
| 4,522,918 | 6/1985 | Schlom et al. | 435/7.23 |
| 4,753,894 | 6/1988 | Frankel et al. | 435/7.23 |

FOREIGN PATENT DOCUMENTS

| | | |
|---|---|---|
| 112093 | 6/1984 | European Pat. Off. |
| 118365 | 9/1984 | European Pat. Off. |
| 221561 | 5/1987 | European Pat. Off. |

OTHER PUBLICATIONS

Burchell, et al., 1984, Intl. J. Cancer, 34:763–768.
Menard, et al., 1983, Biological Abstracts, 76:2135, Abstract No. 19838.
Ciocca, et al., 1982, Chemical Abstracts, 97:355, Abstract No. 159006f.
Olsnes, S., 1981, Nature, 290:84.
Taylor-Papadimitriou, J., et al., 1981, Intl. J. Cancer, 28:17–21.
Yuan, D., et al., 1982, JNCI, 68:719–728.
Ciocca, D. R., et al., 1982, Cancer Research, 42:4256–4258.
Neville, D. M., et al., 1982, Immunol. Rev., 62:75–91.
Ross, W. C. J., et al., 1980, European J. Biochem., 104:381–390.
Vitetta, E. S., et al., 1982, Immunol. Rev., 62:159–183.
Raso, V., et al., 1982, Cancer Research, 4 2:457–464.
Trowbridge, I. W., et al., 1981, Nature (Cond), 294:171–173.
Colcher, D., et al., 1981, PNAS (USA), 78:3199–3203.
Ring, D. B., et al., 1989, Cancer Research, 49:3070–3080.
Sheer, D. G., et al., 1988, Cancer Research, 48:6811–6818.

Primary Examiner—Esther L. Kepplinger
Assistant Examiner—Toni R. Scheiner
Attorney, Agent, or Firm—Gregory J. Giotta; Scott R. Bortner; Philip L. McGarrigle

[57] ABSTRACT

Murine monoclonal antibodies, or fragments thereof, that bind selectively to human breast cancer cells, are IgGs or IgMs, and when conjugated to ricin A chain, exhibit a TCID 50% against at least one of MCF-7, CAMA-1, SKBR-3, or BT-20 cells of less than about 10 nM. Methods for diagnosing, monitoring, and treating human breast cancer with the antibodies or immunotoxins made therefrom are described.

4 Claims, No Drawings

MONOCLONAL ANTI-HUMAN BREAST CANCER ANTIBODIES

CROSS REFERENCE TO RELATED APPLICATIONS

This application is a continuation of U.S. Ser. No. 842,476, filed Mar. 21, 1986, which is a continuation-in-part of U.S. Ser. No 690,750, now U.S. Pat. No. 4,753,894, filed Jan. 11, 1985, which is a continuation-in-part of U.S. Ser. No. 577,976, filed Feb. 8, 1984, now abandoned.

DESCRIPTION

This invention is in the fields of immunology and cancer diagnosis and therapy. More particularly, it concerns murine monoclonal anti-human breast cancer antibodies, hybridomas that produce those antibodies, immunochemicals made from those antibodies, and diagnostic and therapeutic methods that use those immunochemicals.

2. Background Art

Since the mid-1970's, there have been numerous reports of murine monoclonal antibodies that interact with human breast cancer associated antigens. In these reported studies, mice were immunized and boosted with human milk fat globule proteins, breast cancer cell lines or breast cancer membrane extracts. Immune splenocytes were fused with mouse myeloma cells and hybridomas were selected based on some specificity of the culture media for breast or breast cancer antigens. Taylor-Papaddimitriou, J. et al., *Int. J. Cancer* (1981) 28:17-21; Yuan, D., et al., *JNCI* (1982) 68:719-728; Ciocca, D. R., et al., *Cancer Res.* (1982) 42:4256-4258. The normal tissue activities of these prior antibodies are different than the normal tissue reactivities of the antibodies of the present invention.

Numerous prior workers have suggested or reported linking cytotoxic agents or antibodies to make "immunotoxins". Recent interest has centered on immunotoxins of monoclonal antibodies conjugated to the enzymatically active portions (A chains) of toxins of bacterial or plant origin via heterobifunctional agents. Neveill, D. M. and Youle, R. J. *Immunol. Rev.* (1982) 62:75-91; Ross, W. C. J., et al., *European J. Biochem,* (1980) 104; Vitteta, E. S., et al., *Immunol. Rev.* (9182) 62:158-183; Raso, V., et al., *Cancer Res.* (1982) 42:457-464; Trowbridge, I. W. and Domingo, D. L., *Nature(Cond)* (1981) 294:171-173.

DISCLOSURE OF THE INVENTION

A principal aspect of the invention concerns murine monoclonal antibodies that:

(a) bind selectively to human breast cancer cells;
(b) are IgGs or IgMs;
(c) when conjugated to rich A chain exhibit a TCID 50% of less than about 10 mM against at least one of MCF-7, CAMA-1, SKBR-3, or BT-20 cells.

Preferred embodiments of these antibodies are those designated 260F9, 113F1, 2G3, 280D11, 266B2, 33F8, 245E7, 454C11, 317G5, 520C9, and 369F10, and functional equivalents thereof.

The murine x murine hybridomas that produce the above described antibodies and progeny of those hybridomas are other aspects of the invention.

Another aspect of the invention relates to immunotoxins that are conjugates of (a) the above described monoclonal antibodies, and
(b) a cytotoxic moiety.

Another aspect of the invention concerns labeled derivatives of the above described monoclonal antibodies that are labeled with a detectable label that permits the derivatives to be used in diagnosing or monitoring human breast cancer.

Another aspect of the invention concerns a method of killing human breast cancer cells by contacting the cells with a cytocidally effective amount of one or more of the above described immunotoxins.

Other aspects of the invention are direct and indirect immunoassays for determining whether a human cell is a breast cancer cell. These assays involve incubating the cells with the monoclonal antibodies or labeled derivatives thereof. When the labeled derivatives are used, the presence of labeled binary immune complexes on the cells is read directly. When unlabeled antibody is used the cells are further incubated with a labeled antibody against monoclonal antibody and the presence of labeled ternary immune complexes on the cells is read.

MODES FOR CARRYING OUT THE INVENTION

As used herein, the term "monoclonal antibody" means an antibody composition having a homogeneous antibody population. It is not intended to be limited as regards to the source of the antibody or the manner in which it is made.

As used herein with respect to the exemplified murine monoclonal anti-human breast cancer antibodies, the term "functional equivalent" means a monoclonal antibody, fragments thereof, or any molecule having the antigen binding site of the monoclonal antibody that: (a) crossbacks an exemplified monoclonal antibody; (b) binds selectively to human breast cancer cells; (c) has a G or M isotope; (d) binds to the same antigen as determined by immunoprecipitation or sandwich immunoassay; and (e) when conjugated to ricin A chain, exhibits a TCID 50% against at least one of MCF-7, CAMA-1, SKBR-3, or BT-20 cells of less than about 10 mM.

Antibody fragments include the Fab, Fab', and F(ab')$_2$ regions, or derivatives or combinations thereof. Fab, Fab', and F(ab')$_2$ regions of an immunoglobin may be generated by enzymatic digestion of the monoclonal antibodies using techniques well known to those skilled in the art. Fab fragments may be generated by digesting the monoclonal antibody with papain and contacting the digest with a reducing agent to reductively cleave disulfide bonds. Fab' fragments may be obtained by digesting the antibody with pepsin and reductive cleavage of the fragment so produce with a reducing agent. In the absence of reductive cleavage, enzymatic digestion of the monoclonal with pepsin produces F(ab')$_2$ fragments.

It will further be appreciated that encompassed within the definition of monoclonal antibody is single chain antibody that can be generated as described in U.S. Pat. No. 4,704,692, as well as hybrid antibodies described in U.S. patent application Ser. No. 474,893 and by Munroe, (1984) *Nature* 312:597; Morrison, S. L. (1985) *Science* 229:1202 and Oi, et al. (1986) *Biotechniques* 4:214. Particularly useful hybrid antibodies are "humanized" antibodies made as described in European Patent Application No. 302,620. These publications are hereby incorporated by reference.

As used herein with regard to the monoclonal antibody-producing hybridomas of the invention, the term "progeny" is intended to include all derivatives, issue, and offspring of the parent hybridoma that produce the monoclonal anti-human breast cancer antibody produced by the parent, regardless of generation of karyotypic identify.

Monoclonal Antibody Production

The antibody-producing fusion partners that are used to make the hybridomas of this invention are generated by immunizing mice with live human breast cancer cells or membrane extracts made therefrom. The mice are inoculated intraperitoneally with an immunogenic amount of the cells or extract and then boosted with similar amounts of the immunogen. Spleens are collected from the immunized mice a few days after the final boost and a cell suspension is prepared therefrom for use in the fusion.

Hybridomas are prepared from the spenocytes and a murine tumor partner using the general somatic cell hybridization technique of Kohler, B. and Milstein, C., Nature (1975) 256:495–497 as modified by Buck, D. W., et al., In Vitro (1982) 18:377–381. Available murine myeloma lines, such as those from the Salk Institute, Cell Distribution Center, San Diego, Calif., USA, may be used in the hybridization. Basically, the technique involves fusing the tumor cells and splenocytes using a fusogen such a polyethylene glycol, or by electrical means well known to those skilled in the art. After the fusion the cells are separated from the fusion medium and grown in a selective growth medium, such as HAT medium, to eliminate unhybridized parent cells. The hybridomas are expanded, if desired, and supernatants are assayed for antihuman breast cancer activity by conventional immunoassay procedures (e.g., radioimmunoassay, enzynme immunoassay, or fluoroescence immunoassay using the immunizing agent (breast cancer cells or membrane extract) as antigen. Positive clones are characterized further to determine whether they meet the criteria of the invention antibodies.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precipitation, gel electrophoresis, dialysis, chromatography, and ultrafiltration, if desired.

Monoclonal Antibody Selection/Characterization

The important characteristics of the monoclonal antibodies are (1) their immunoglobulin class, (2) their selectivity for human breast cancer cells and the range of human breast cancer cells to which they bind and (3) their usefulness in making effective anti-human breast cancer immunotoxins.

The selectivity and range of a given antibody is determined by testing it against panels of (1) human breast cancer tissues and cells and (2) normal human tissues or cells of breast or other origin. In selecting the claimed antibodies approximately twenty-two thousand growing hybridoma cultures were initially screened against the immunizing breast tumor membranes, a fibroblast cell line and a breast tumor frozen section. Clones that reacted with the neoplastic materials but not the normal materials were identified in this initial screen and chosen for isotyping and additional screening for selectivity and range. The additional screening involved: sixteen normal tissue sections, five normal blood cell types, eleven nonbreast neoplasm sections, twenty-one breast cancer sections and fourteen breast cancer cell lines. Antibodies were deemed to bind selectively to breast cancer if they bound strongly to less than about $\frac{1}{3}$ of the normal tissues and blood cell types. One hundred twenty-seven antibodies were purified and tested on the additional screen.

Antibodies exhibiting acceptable selectivity and range were conjugated to ricin A chain using N-succinimidyl-3-(2-pyridyldithio)propionate (SPDP) or iminothiolane (IT) as a coupling agent. The conjugates were tested against MCF-7, CAMA-1, SKBR-3, and BT-20 cells in a 24-hour tissue culture assay. Sixteen of the antibodies exhibited acceptable immunotoxin activity (TCID 50% of less than 10 nM) against at least one of these breast tumor lines. Seven of the sixteen were found to recognize the same 210,000 dalton antigen, with six of the seven probably recognizing the same epitope but differing in affinity.

Further details of the characterization of these antibodies are provided in the examples below.

Immunochemicals

The immunochemical derivatives of the monoclonal antibodies of this invention that are of prime importance are immunotoxins (conjugates of the antibody and a cytotoxic moiety) and labeled (e.g., radiolabeled, enzymelabeled, or fluorochrome-labeled) derivatives in which the label provides a means for identifying immune complexes that include the labeled antibody.

The cytotoxic moiety of the immunotoxins may be a cytotoxic drug or an enzymatically active toxin of bacterial or plant origin, or an enzymatically active fragment ("A chain") of such a toxin. Enzymatically active toxins and fragments thereof are preferred and are exemplified by diptheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), momordica charantia inhibitor, curcin, crotin, saponaria officinalis inhibitor, gelonin, mitogellin, restrictocin, phenomycin, and enomycin. Ricin A chain, nonbinding active fragments of diptheria toxin, abrin A chain, and PAPII are preferred. Conjugates of the monoclonal antibody and such cytotoxic moieties may be made using a variety of bifunctional protein coupling agents. Examples of such reagents are SPDP, IT, bifunctional derivatives of imidoesters such as dimethyl adipimidate. HCl, active esters such as disuccinimidyl suberate, aldehydes such as glutaraldehyde, bis-azido compounds such as bis(p-azidobenzoyl) hxanediamine, bis-diazonium derivaties such as bis-(p-diazoniumbenzoyl)-ethylenediamine, diisocyanates such as tolylene 2,6-diisocyanate, and bis-active fluorine compounds such as 1,5-difluoro-2,4-dinitrobenzene.

When used to kill human breast cancer cells in vitro for diagnostic purposes, the conjugates will typically be added to the cell culture medium at a concentration of at least about 10 nM. The formulation and mode of administration for in vitro use are not critical. Aqueous formulations that are compatible with the culture or perfusion medium will normally be used. Cytotoxicity may be ready by conventional techniques to determine the presence or degree of breast cancer.

When used in vivo for therapy, the immunotoxins are administered to the patient in therapeutically effective amounts (i.e., amounts that eliminate or reduce the patient's tumor burden). They will normally be administered parenterally, preferably intravenously, although other routes may be employed and even preferred depending on the nature and site of the tumor (i.e., intratumoral administration). The dose and dosage regimen will depend upon the nature of the cancer (primary or metastatic) and is population, the characteristics of the particular immunotoxin, e.g., it therapeutic index, the patient, and the patient's history. The amount of immunotoxin administered will typically be in the range of about 0.1 to about 10 mg/kg of patient weight.

For parenteral administration the immunotoxins will be formulated in a unit dosage injectable form (solution, suspension, emulsion) in associated with a pharmaceutically acceptable parenteral vehicle. Such vehicles are inherently nontoxic and nontherapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicles may contain minor amounts of additives such as substances that enhance isotonicity and chemical stability, e.g., buffers and preservatives. The immunotoxins will typically be formulated in such vehicles at concentrations of about 1mg/ml to 10 mg/ml.

Cytotoxic radiopharmaceuticals for treating breast cancer may be made by conjugating high linear energy transfer (LET) emitting isotopes (e.g., Y, Pr) to the antibodies. The term "cytotoxic moiety" as used herein as intended to include such isotopes.

The labels that are used in making labeled versions of the antibodies include moieties that may be detected directly, such as fluorochromes and radiolabeled, as well as moieties, such as enzymes, that must be reacted or derivatized to be detected. Examples of such labels are $^{32}P$, $^{125}I$, $^{3}H$, $^{14}C$, fluorescein and its derivatives, rhodamine and its derivatives, dansyl, umbelliferone, luciferia, 2,3-dihydrophthalazinediones, horseradish peroxidase, alkaline phosphatase lysozyme, and glucose-6-phosphate dehydrogenase. The antibodies may be tagged with such labels by known methods. For instance, coupling agents such as aldehydes, carbodiimides, dimaleimide, imidates, succinimides, bis-diazotized benzidine and the like may be used to tag the antibodies with the above-described fluorescent, chemiluminescent, and enzyme labels.

The antibodies and labeled antibodies may be used in a variety of immunoimaging or immunoassay procedures to detect the presence of breast cancer in a patient or monitor the status of such cancer in a patient already diagnosed to have it. When used to monitor the status of a caner a quantitative immunoassay procedure may be used. Such monitoring assays are carried out periodically and the results compared to determine whether the patient's tumor burden has increased or decreased. Common assay techniques that may be used include direct and indirect assays. Direct assays involve incubating a tissue sample or cells from the patient with a labeled antibody. If the sample includes breast cancer cells, the labeled antibody will bind to those cells. After washing the tissue or cells to remove unbound labeled antibody, the tissue sample is read for the presence of labeled immune complexes. In indirect assays the tissue or cell sample is incubated with unlabeled monoclonal antibody. The sample is then treated with a labeled second antibody (or antibody fragment) against the monoclonal antibody (e.g., a labeled antimurine antibody or fragment), washed, and read for the presence of labeled ternary complexes.

For diagnostic use the antibodies will typically be distributed in kit form. These kits will typically comprise: the antibody in labeled or unlabeled form in suitable containers, reagents for the incubations and washings, a labeled antimurine antibody if the kit is for an indirect assay, and substrates or derivatizing agents depending on the nature of the label. Human breast cancer antigen controls and instructions may also be included.

The following examples provide a detailed description of the preparation, characterization, and use of representative monoclonal antibodies of this invention. These examples are not intended to limit the invention in any manner.

Immunization

Fresh postsurgical human breast cancer tissue and a variety of normal tissues were used to prepare membrane extracts by Polytron homogenization and disconTinuous suscrose gradient centrifugation. Human breast cancer cell lines were obtained from the Breast Caner Task Force, the American Type Culture Collection (ATCC), and from Dr. Jorgen Fogh at Memorial Sloan Kettering. The cells were maintained and passaged as recommended by the Breast Cancer Task Force, the ATCC and Dr. Fogh. For immunizations, either membrane extract containing 100 µg of protein (Lowry assay) or ten million live breast cancer cells were inoculated intraperitoneally into five week old Balb/c mice. The mice were boosted identically twice at monthly intervals. Three days after the 1st boost, the spleens were removed for cell fusion.

Hybridoma Methods

Hybridoma supernatant was assayed for reactive antibody in either a solid phase enzyme-linked immunosorbent assay (ELISA) with the immunizing breast cancer membrane extract or an indirect immunofluorescence assay with the immunizing breast cancer cell line. For the solid phase membrane ELISA, 40 µl of 0.1 mg/ml breast cancer membrane protein were placed in polyvinyl chloride (PVC) microtiter wells (Dynatech, Inc.) for 12 hours at 4° C. The extract was aspirated and the wells washed with phosphate buffered saline (PBS) containing 1% bovine serum albumin (BSA). The wells were the incubated with 45 µl of a 1:10 dilution of hybridoma supernatant. The diluent was RPMI 1640 media with 25 mM Hepes, 10% bovine serum, and 0.1% sodium azide. After 30 minutes at room temperature, the wells were again washed and incubated 45 minutes at 37° C. with a 1:200 dilution of peroxidase conjugated goat anti-mouse IgG (Zymed, Inc.). The diluent was PBS. The wells were then washed with PBS and reacted with 200 µl of 2,2-azino-di(3-ethylbenzthiazoline supphonic acid) in 0. 1sodium citrate buffer pH 4.2 for 30 minutes at room temperature. Optical density was measured at 405 mm on a MicroElisa Reader (Dynatech, Inc.). For each experiment a positive control, anti-beta 2 microglobulin at 5 µg/ml (Becton Dickinson, Inc.), was reacted with normal human kidney membrane. This gave an optical density of 1.0±0.1 (standard deviation). The background was 0±0.1 optical density units (O.D.) using media without mouse monoclonal antibody. Wells that gave a reaction on the breast cancer membrane extract of greater than 0.7 O.D. were saved. For the indirect immunofluorescence cell line assay was placed one hundred thousand breast cancer cells of the immunizing cell line overnight with appropriate media in each chamber of a set of eight chambered slides (Lab-tek, Inc.). Similarly, one hundred thousand fibroblast cells from cell line CC05 were incubated overnight in chambered slide wells. The cells were washed with PBS containing 1% BSA (Miles, Inc.). The wells, both breast cancer and fibroblast, were incubated 30 minutes at 4° C. with a 1:50 dilution of fluorescein isothiocyanate (FITC)-conjugated goat F(ab')$_2$ anti-mouse Ig (Zymed, Inc.). The cells were washed three times, fixed in 1.5% formaldehyde in PBS for five minutes, chambers removed and rinsed in PBS. The slides were then mounted in Aguamount (Lenex Lab) and examined with a Laborlus 12 fluorescence microscope (Leitz, Inc.) Hybridoma wells showing strong fluorescent binding to breast cancer cells but no fluorescent binding to fibroblasts were saved. Five thousand one hundred fifty-six hybridoma wells revealed breast cancer reactivity in the initial screen.

Supernatants from the 5156 positive wells were then tested in solid phase ELISA with eight normal tissue membrane extracts (liver, lung, colon, stomach, kidney, tonsil, spleen and pancrease). Any well supernatant giving an ELISA O.D. greater than 0.3 was discarded. One thousand one hundred one of the supernatants were found to be unreactive with the normal tissue extracts.

The 1101 hybridoma supernatants were tested on frozen sections of human breast carcinoma tissues. Six micron sections were attached to slide, fixed 10 minutes in acetone at 4° C., dried 10 minutes at room temperature, washed with PBS, blocked with horse serum and incubated 20 minutes at room temperature with 200 μl neat hybridoma supernatant. The slides were washed with PBS, and finally incubated 20 minutes at 37° C. with a 1:50 dilution of peroxidase conjugated rabbit anti-mouse Ig (Tago, Inc.), washed again with PBS, and finally incubated 7.5 minutes at 37° C. with 0.5 mg/ml diaminobenzidine (Sigma, Inc.) in 0.05 M Tris buffer pH 7.2 containing 0.01% hydrogen peroxide (Fisher, Inc.). The slides were stained with hematoxylin, dehydrated and mounted in Permount (Fisher, Inc.). One hundred twenty-four wells yielded breast cancer selective binding and were cloned.

Purification and Class Determination

Immunoglobulin class and subclass of the monoclonal breast cancer selective antibodies were determined. Antibodies were also internally labeled by growing 2–3×10$_6$ hybridoma cells for four hours in methionine-free medium containing 0.2 μCi $^{35}$S methionine (New England Nuclear). $^{35}$S-labeled antibodies were immunoprecipitated with fixed staphylococcus A cells (IgSorb, The Enzyme Center) or with IgSorb precoated with rabbit anti-mouse immunoglobulin (Zymed), and the imnmunoprecipitates were analyzed by SDS-PAGE to determine antibody light and heavy chain mobility, lack of extra chains, and the ability of each antibody to bind staphylococcal protein A.

The antibodies were expanded in vivo. Balb/c or F1 (C578/6×Balb/c) mice were primed with 0.5 ml pristine intraperitoneally (ip) and after 10–14 days inoculated with one million log phase hybridoma cells in PBS. Ascites fluid was stored at −70° C. and thawed and filtered through a 0.8 micron Millex filter unit before further purification.

IgG antibodies that bound staphylooccal protein A were purified by affinity chromatography on protein A-sepharose (Pharmacia) with pH step gradient elution. IgG antibodies that did not bind protein A were precipitated by addition of ammonium sulfate to 40% saturation at 0° C. The precipitates were redissolved in PBS, dialysed to 20 mM Tris pH 7.2 and chromatographed on a 1.6×50 cm column of diethylaminoethyl cellulose (DEAE) Affi-Gel Blue (BioRad) eluting with a 1.5 liter (0–600 mM NaCl gradient at 4° C. at a flow rate of 1 ml/min. In each case, column fractions were monitored by SDS-PAGE and the purest antibody fractions were pooled, concentrated to 1–3 mg/ml, dialysed to PBS/0.02% NaN$_3$, and stored at 40° C.

IgM antibodies were purified by gel filtration on a 2.6×40 cm column of Sephacryl S-300 (Pharmacia) eluting with PBS/0.01% sodium azide at room temperature at a flow rate of 1 ml/min.

Selectivity Determination

In order to evaluate their selectivity for breast cancer, the purified antibodies were tested by immunoperoxidase section staining on sections of sixteen normal tissues, and by immunofluorescent cell sorting on five blood cell types. Immunoperoxidase staining was performed as above except that known dilutions of purified antibodies in PBS in the range of 1–40 μg/ml were used instead of hybridoma supernatants. The pure antibodies were first titrated to find the minimal concentration giving strong immunoperoxidase staining on breast cancer sections and then used at that concentration for the normal tissue tests. Peripheral blood cells (platelets, lymphocytes, red blood cells, granulocytes, and monocytes) were prepared by centrifugation using Mono-Poly Resolving Medium (Flow Laboratories), Inc.). The cells were reacted with antibody at the optimal concentration determined above for 30 minutes at 4° C., washed, reacted with a 1:50 dilution of FITC-conjugated goat anti-mouse Ig (Tago, Inc.) for 30 minutes at 4° C., washed again and examined in an EPICS cell sorter (Coulter Electronics, Inc.). The buffer and diluents were PBS with 1% gelatin and 0.02% sodium azide. The EPICS V was equipped with a 76 micron nozzle and a one watt argon ion laser at 488 nm. An 80 mm confocal lens was used on the optical rail assembly for focusing. Other filters used were a 515 nm interference filter and a 515 mm absorbance filter (for scattered laser light) and a neutral density 1.5 filter (Melles Griot) for forward angle light scatter. Contour plots of log fluorescein fluorescence versus forward angle light scatter were used for sample analysis.

The binding behaviors of the claimed antibodies are reported in Table 1 below.

TABLE 1

| ANTIBODY BINDING TO NORMAL TISSUE SECTIONS | | | | | | | | | | | | | | | | |
|---|---|---|---|---|---|---|---|---|---|---|---|---|---|---|---|---|
| | | | | | | | Tissue | | | | | | | | | |
| Antibody | Pancrea | Esophagus | Lung | Kidney | Colon | Stomach | Brain | Tonsil | Liver | Heart | Ovary | Skin | Breast | Bone | Uterus | Bladder |
| 33F8 | 0 | 2E | 0 | 1T | 0 | 0 | 0 | 1Ly | 0 | 0 | 0 | 1W | 0 | 1Mk | 1L | 1E |

TABLE 1-continued

ANTIBODY BINDING TO NORMAL TISSUE SECTIONS

| Antibody | Pancrea | Esophagus | Lung | Kidney | Colon | Stomach | Brain | Tonsil | Liver | Heart | Ovary | Skin | Breast | Bone | Uterus | Bladder |
|---|---|---|---|---|---|---|---|---|---|---|---|---|---|---|---|---|
| 113F1 | 2Ac | 2E | 0 | 0 | 0 | 2G | 0 | 1E | 0 | 0 | 0 | 0 | 0 | 0 | 0 | 1E |
| 245E7 | 1L | 0 | 1A, M | 0 | 0 | 2L | 0 | 1E | 0 | 0 | 0 | 2S | 2L | 0 | 2L | 1E |
| 2G3 | 2Ac | 2E | 1A | 2T | 0 | 1L | 0 | 1E | 0 | 0 | 0 | 0 | 2E | 0 | 2L | 2E |
| 260F9 | 1Ac | 2E | 0 | 1T | 0 | 1G | 0 | 2E | 2D | 0 | 0 | 2E, 2H | 2E | 0 | 1L | 2E |
| 280D11 | 0 | 1E | 0 | 2T, 2B | 1L | 2L | 0 | 0 | 2D | 0 | 0 | 1E, 1H | 2L | 2Gr | 2G | 0 |
| 266B2 | 1Ac, 1D | 2E | 0 | 1T | 0 | 0 | 0 | 2E | 0 | 0 | 0 | 2E, 2W | 1E | 0 | 0 | 1E |
| 454C11 | 1D | 1-2E | 0 | 1T | 0 | 0 | 0 | 1E | 1D | 0 | 0 | 1E, H | 1E | 0 | 1G | 1E |
| 317G5 | 1Ac, 1 | 0 | 0 | 2T | 1G | 0 | 0 | 0 | 2D | 0 | 0 | 0 | 0 | 0 | 1G | 0 |
| 520C9 | 0 | 0 | 0 | 1T | 0 | 0 | 0 | 0 | 0 | 0 | 0 | 0 | 0 | 0 | 0 | 0 |
| 452F2 | 0 | 0 | 0 | 0 | 0 | 0 | 0 | 0 | 0 | 0 | 0 | 0 | 0 | 0 | 0 | 0 |
| 369F10 | 0 | 0 | 0 | 0 | 0 | 1G | 0 | 0 | 0 | 0 | 0 | 1S | 0 | 0 | 0 | 0 |
| 736G9 | 0 | 0 | 0 | 0 | 0 | 0 | 0 | 0 | 0 | 0 | 0 | 0 | 0 | 0 | 0 | 0 |
| 741F8 | 0 | 0 | 0 | 0 | 0 | 0 | 0 | 0 | 0 | 0 | 0 | 0 | 0 | 0 | 0 | 0 |
| 758G5 | 0 | 0 | 0 | 1T | 0 | 0 | 0 | 0 | 0 | 0 | 0 | 0 | 0 |  | 0 | 0 |
| 761B10 | 0 | 0 | 0 | 1T | 0 | 0 | 0 | 0 | 0 | 0 | 0 | 0 | 0 |  | 0 | 0 |

Staining intensity: 2 = strong; 1 = weak; 0 = negative.
A = alveolar cells; Ac = acini; B = Bowman's capsule; D = ducts; E = epithelial; G = granulocytes; B = hair follicles; I = islets; L = umen ± apical cytoplasm; Ly = lymphocytes; M = macrophages; Mk = megakonyocytes; My = myelin; S = stroma; T = tubules; U = glomeruli; W = sweat glands.
There was no binding to platelets, red cells, lymphocytes, monocytes or granulocytes except 280D11 weakly binding granulocytes. None of the antibodies bound fibroblasts.

In order to determine how wide a range of breast cancer might be recognized by each antibody, the breast cancer selective antibodies were tested by immunoperoxidase staining on frozen sections of 27 different breast tumors. The breast cancers used for section staining were all infiltrating intraductal carcinomas, so no correlation of antibody binding with histologic type of breast cancer could be made. In addition, no correlation between antibody biding and the nodal status or estrogen receptor status was found for the twelve tumors for which donor information was available. Antibodies reacted equally well with metastatic and primary breast tumors. The results of these tests for the claimed antibodies are reported in Table 2 below.

TABLE 2

ANTIBODY BINDING TO BREAST CANCER TISSUE SECTIONS*

| Antibody | LA | KA | JA | IA | HA | GA | E | EA | TA | UA | RA | SA | O | R |
|---|---|---|---|---|---|---|---|---|---|---|---|---|---|---|
| 2G3 | 1 | 2 | 1 | 2 | 2 | 2 | ND | 2 | 2 | 2 | 2 | 2 | 2 | 2 |
| 33F8 | 1 | 1 | 0 | 0 | 0 | 0 | 1 | 0 | 0 | 0 | 0 | 0 | 1 | 0 |
| 113F1 | 0 | 1 | 1 | 0 | 0 | 0 | 0 | 0 | 0 | 0 | 1 | 0 | 0 | 0 |
| 245E7 | 2 | 2 | 2 | 2 | 2 | 2 | 2 | 2 | 2 | 2 | 2 | 2 | 2 | 2 |
| 260F9 | 0 | 1 | 0 | 1 | 0 | 1 | ND | 1 | 2 | 0 | 0 | 0 | 1 | 0 |
| 280D11 | 2 | 2 | 0 | 1 | 2 | 1 | ND | 1 | 1 | 0 | 1 | 0 | 1 | 1 |
| 266B2 | 1 | 2 | 0 | 1 | 0 | 1 | ND | 0 | 2 | 1 | 1 | 0 | 1 | 0 |
| 454C11 | 1 | 2 | 0 | 2 | 1 | 1 | ND | 2 | 1 | 1 | 0 | 0 | ND | 0 |
| 317G5 | 1 | ND | 0 | 0 | 1 | ND | ND | 0 | 0 | 0 | 1 | 1 | ND | 0 |
| 520C9 | 0 | ND | 0 | 2 | 0 | ND | ND | 2 | 0 | 1 | 0 | 0 | ND | 0 |
| 452F2 | 0 | 2 | 0 | 2 | 0 | 0 | ND | 1 | 0 | 1 | 0 | 0 | ND | 0 |
| 369F10 | 2 | 2 | 2 | 2 | 0 | 0 | ND | 1 | 0 | 1 | 1 | 2 | 2 | 0 |
| 736G9 | 2 | ND | 0 | 2 | 0 | ND | ND | 1 | 0 | 1 | 0 | 0 | ND | 0 |
| 741F8 | 0 | ND | 0 | 2 | 0 | ND | ND | 2 | 0 | 1 | 0 | 0 | 0 | 0 |
| 758G5 | 1 | ND | 0 | 0 | 0 | ND | ND | 2 | 0 | 1 | 0 | 0 | ND | 0 |
| 761B10 | 1 | ND | 0 | 2 | 0 | ND | ND | 2 | 0 | 1 | 0 | 0 | ND | 0 |

| Antibody | MA | BA | NA | FA | LMA | LME | MBA | Z | YA | KB | CB | IC | EC |
|---|---|---|---|---|---|---|---|---|---|---|---|---|---|
| 2G3 | 1 | 2 | 2 | 2 | 2 | 2 | 2 | 2 |  |  |  |  |  |
| 33F8 | 0 | 0 | 0 | 0 | 0 | 0 | 0 | ND |  |  |  |  |  |
| 113F1 | 0 | 0 | 0 | 0 | 0 | 0 | 0 | ND |  |  |  |  |  |
| 245E7 | 2 | 2 | 2 | 2 | 2 | 2 | 2 | ND |  |  |  |  |  |
| 260F9 | 0 | 1 | 1 | 1 | 0 | 1 | 1 | 0 |  |  |  |  |  |
| 280D11 | 1 | 1 | 0 | 1 | 0 | 1 | 1 | 1 |  |  |  |  |  |
| 266B2 | 1 | 1 | 2 | 1 | 0 | 1 | 1 | 1 |  |  |  |  |  |
| 454C11 | 2 | 0 | 0 | 1 | 0 | 1 | 1 | ND |  |  |  |  |  |
| 317G5 | 1 | 0 | 1 | 1 | 0 | 0 | 0 | 0 | 0 | 1 | 1 |  |  |
| 520C9 | 2 | 0 | 1 | 0 | 0 | 0 | 0 | 0 |  |  |  |  |  |
| 452F2 | 1 | 0 | 0 | 0 | 0 | 0 | 0 | 0 |  |  |  |  |  |
| 369F10 | 0 | 2 | 2 | 2 | 2 | 2 | 2 | 1 |  |  |  |  |  |
| 736G9 | 1 | 0 | 0 | 0 | 0 | 0 | 0 | 0 | 0 | 0 | 0 |  |  |
| 741F8 | 2 | 0 | 0 | 0 | 0 | 0 | 0 | 0 | 0 | 0 | 0 |  |  |
| 758G5 | 2 | 0 | 0 | 1 | 0 | 0 | 0 | 0 | 1 | 0 | 1 |  |  |
| 761B10 | 2 | 0 | 0 | 0 | 0 | 0 | 0 | 0 | 0 | 0 | 1 |  |  |

*Staining intensity: 2 = strong; 1 = weak; 0 = negative; ND—not determined.

Antibodies were further evaluated for range of breast cancer recognition by cell line immunofluorescence assays on 14 breast cancer cell lines. Table 3 below reports the results of these tests for the claimed antibodies.

TABLE 3
ANTIBODY BINDING TO BREAST CANCER CELL LINES*

| Antibody | SKBr3 | BT483 | MCF7 | BT20 | ZR751 | MDAMB231 | CAMA1 |
|---|---|---|---|---|---|---|---|
| 2G3 | + | + | + | + | + | + | + |
| 33F8 | + | + | + | + | + | − | + |
| 113F1 | + | + | + | + | + | + | + |
| 245E7 | + | + | + | + | + | + | + |
| 260F9 | + | + | + | + | + | + | + |
| 280D11 | + | + | + | + | + | − | + |
| 266B2 | + | + | + | + | + | + | + |
| 454C11 | + | + | + | + | + | + | + |
| 520C9 | + | + | − | − | − | NT | + |
| 452F2 | + | + | − | − | + | NT | + |
| 369F10 | − | + | − | − | − | − | + |
| 736G9 | + | + | − | NT | NT | NT | + |
| 741F8 | + | + | − | NT | NT | NT | + |
| 758G5 | + | + | − | NT | NT | NT | − |
| 761B10 | + | + | − | NT | NT | NT | − |

| Antibody | ALAB | BT549 | BT474 | T47D | MDAMB157 | MDAMB330 | ZR7530 |
|---|---|---|---|---|---|---|---|
| 2G3 | + | + | + | + | + | − | + |
| 33F8 | + | + | + | − | + | + | − |
| 113F1 | − | − | + | + | + | + | − |
| 245E7 | + | + | + | + | + | − | + |
| 260F9 | + | − | + | + | + | + | + |
| 280D11 | − | + | + | + | + | − | + |
| 266B2 | − | − | + | + | − | + | + |
| 454C11 | + | − | NT | − | NT | NT | + |
| 520C9 | NT | − | NT | − | NT | NT | + |
| 452F2 | + | − | NT | − | NT | NT | + |
| 369F10 | − | − | NT | − | NT | NT | − |
| 736G9 | NT | − | NT | + | NT | NT | + |
| 741F8 | NT | − | NT | + | NT | NT | + |
| 758G5 | NT | − | NT | − | NT | NT | + |
| 761B10 | NT | − | − | NT | + | NT | + |

*Cell line binding: + = positive; − = negative; NT = not tested.

Finally, the antibodies were tested by immunoperoxidase staining on 11 non-breast malignancies. The results for the claimed antibodies are reported in Table 4 below.

TABLE 4
ANTIBODY BINDING TO CANCERS*

| Antibody | Colon | Lung | Prostate | Pancreas | Uterine | Lymphoma | Stomach | Bladder | Esophagus | Melanoma | Ovarian |
|---|---|---|---|---|---|---|---|---|---|---|---|
| 2G3 | 2 | 0 | 2 | 0 | 2 | 0 | 2 | 0 | 0 | 2 | 2 |
| 33F8 | 0 | 1 | 0 | 0 | 1 | 0 | 0 | 0 | 0 | 0 | 1 |
| 113F1 | 0 | 2 | 0 | 2 | 1 | 2 | 2 | 0 | 1 | 0 | 1 |
| 245E7 | 0 | 2 | 2 | 2 | 2 | 2 | 0 | 0 | 0 | 0 | 2 |
| 260F9 | 0 | 0 | 1 | 1 | 1 | 0 | 0 | 0 | 1 | 0 | 2 |
| 266B2 | 0 | 1 | 1 | 1 | 1 | 0 | 1 | 0 | 1 | 0 | 1 |
| 280D11 | 0 | 0 | 1 | 1 | 1 | 2 | 0 | 0 | 0 | 0 | 2 |
| 454C11 | 0 | 0 | 1 | 1 | 2 | 0 | 0 | 0 | 0 | 0 | 1 |
| 317G5 | 1 | 1 | 0 | 0 | 1 | 0 | 0 | 0 | 0 | 0 | 0 |
| 520C9 | 0 | 1 | 1 | 1 | 1 | 0 | 0 | 0 | 0 | 0 | 0 |
| 452F2 | 0 | 0 | 0 | 0 | 0 | 0 | 0 | 0 | 0 | 0 | 0 |
| 369F10 | 0 | 1 | 1 | 1 | 0 | 0 | 0 | 0 | 0 | 0 | 2 |
| 736G9 | 0 | 0 | 0 | 0 | 0 | 0 | 0 | 0 | 0 | 0 | 0 |
| 741F8 | 0 | 0 | 0 | 0 | 0 | 0 | 0 | 0 | 0 | 0 | 0 |
| 758G5 | 0 | 1 | 0 | 0 | 0 | 0 | 0 | 0 | 0 | 0 | 0 |
| 761B10 | 0 | 0 | 0 | 0 | 0 | 0 | 0 | 0 | 0 | 0 | 0 |

*Staining intensity: 2 = strong; 1 = weak; 0 = negative. Only one tumor of each type examined.

Cytotoxicity Evaluation

The claimed antibodies were conjugated to ricin toxin A chain (RTA) treated with SPDP as described by Carlsson, J., et al., Biochem. J. (1978) 173:723–737 or with iminothiolane (IT).

SPDP Conjugation

SPDP (20 mM in ethanol) was added in a 20-fold molar excess to antibody and following a 30 minute incubation at room temperature, the unreacted SPDP was removed by dialysis against PBS. The extent of derivatization was determined by measuring the release of pyridine-2-thione at 343 nm after reduction with dithiothreitol (DTT). Depending on the antibody, three to eight lysine amino acid groups (per antibody molecule) molecule) were converted to the pyridyl-disulfide derivative.

The SPDP-treated antibodies were conjugated with RTA. Immediately prior to conjugation, the RTA was reduced with 50 mM DTT, then desalted on a Sephadex G-25 column to remove DTT from protein. Reduced RTA was added in a three- to five-fold molar excess over pyridyl-disulfide antibody. A typical reaction mixture (1 ml) consisted of 7 μM antibody and 30 μM RTA. The reaction was allowed to proceed overnight at 4° C. The extent of conjugation of RTA to antibody was determined spectrophotometrically by measuring the release of pyridine-2-thione. On the average, conjugates contained two to three RTA molecules per antibody molecule. This was confirmed by nonreducing SPS-PAGE gels (7.5%), which also revealed that the typical conjugate preparation contained 10%-30% free antibody.

The conjugate mixture was chromatographed on the HPLC size exclusion column (TSK-250, BioRad) to separate conjugates from residual unreacted RTA. The column was equilibrated in 0.1 M sodium sulfate/0.02 M sodium phosphate pH 6.8. Conjugate mixture (0.7 ml) was injected, then chromatographed at flow rate of 1 ml/min. (room temperature). Fractions of 0.5 ml were collected and the peak conjugate fractions were pooled and filter sterilized prior to cytotoxicity testing.

Iminothiolane Conjugation

Approximately 30 mg/ml antibody in 0.10 M Na phosphate, 0.001 M Na EDTA, pH 8.0 (hereafter referred to as P-EDTA buffer) is reacted with 1 mM 5,5'-dithiobis-(2-nitrobenzoic acid) (DTNB) at room temperature for about 15 minutes and then chilled to 0° C. in an ice bath. Enough IT is added to this solution to give 2.5 IT molecules/antibody molecule, and the resulting solution is stored at 0°-5° C. for approximately 24 hours. Then it is dialyzed at 0°-5° C. against three 100-fold excess volumes of P-EDTA buffer.

RTA, normally stored in P-EDTA containing 1 mM DTT, is ultrafiltered to a concentration between 10 and 15 mg/ml and dialyzed at 0°-5° C. against three 100-fold excess volumes of P-EDTA. Enough RTA is added to the derivatized antibody to give 1.0-1.2 free thiols on RTA/blocked thiol on derivatized antibody. This mixture is incubated at room temperature for two hours.

The coupling reaction mixture is applied to a column of Blue Trisacryl M (LKB Instruments) which is then eluted with P-EDTA at room temperature. The column is scaled to contain approximately 2 ml of bed volume per mg of starting antibody. After an initial peak of unconjugated antibody has been eluted from the column, the eluant is switched to P-EDTA containing 1 M NaCl. Immunoconjugate and unreacted RTA are eluted in this buffer as a very sharp peak, which is pooled and dialyzed at 0°-5° C. against one 10-fold excess volume of 0.15 M Na phosphate, pH 7.1 (hereafter referred to as $P_i$ buffer). The dialyzed protein is applied to a column of Ultrogel ACA-44 (LKB Instruments) at 0°-5° C. and eluted with buffer at a flow rate of 6 cm/hr. The column is scaled to contain at least 25 ml of bed volume/ml of applied protein. Immunoconjugate is eluted as a single peak, slightly after the excluded volume, baseline-resolved from following peaks of dimerized and monomeric RTA. The pooled immunoconjugate peak is ultrafiltered (amicon YM-100 membrane at 35 psi) to a final concentration of 5.0 mg/mo and filter-sterilized with a Gelmann 0.2 μm Acrodisc.

Cytotoxicity Tests

The test human breast cancer lines used in the cytotoxicity tests were MCF-7, CAMA-1, SKBR-3, and BT-20. The human fibroblast cell lines CC95 and WI-38 were used as negative controls.

Forth thousand test cells in 1 ml medium were added to a set of 8 ml glass vials, followed by the addition of conjugate dilutions (in PBS containing 100 μg/ml BSA). After incubation at 37° C. for 22 hours, the medium was aspirated, the monolayers were washed with PBS, and methionine-free medium supplemented with $^{35}S$ methionine was added. The vials were further incubated two hours at 37° C., the medium was removed, and the cells were washed twice with 2 ml of 10% trichloroacetic acid containing 1 mg/ml methionine. The cells were dried, scintillation fluid was added, and the radioactivity was counted in a scintillation counter. Cytotoxicity was expressed as the tissue culture inhibitory dose of conjugate that resulted in 50% of control (untreated) protein synthesis (TCID 50%).

The results of these cytotoxicity tests are reported in Table 5 below. Not shown are the results for conjugates of $Fab'_2$ fragments of the monoclonals 520C9 and 280D11 which can be expected to have a TCID 50% for the above breast cancer cell lines of less than about 10 mM.

TABLE 5

CYTOTOXICITY OF BREAST TUMOR IMMUNOTOXINS

| | | TCID 50% (nM) | | | | | |
|---|---|---|---|---|---|---|---|
| Conjugate | Isotype | MCF-7 | CAMA-1 | SKBR-3 | BT-20 | CC95 | WI-38 |
| 260F9 | G1 | 0.1 | 0.4 | 0.06 | 9 | >50 | >50 |
| 317G5 | G1 | 0.4 | 5 | 10 | 2 | >50 | >50 |
| 113F1 | G3 | 0.5 | 0.6 | 10 | 6 | >50 | >50 |
| 2G3 | G1 | 0.8 | 1 | >50 | 15 | >50 | >50 |
| 266B2 | G1 | 1 | 5 | 0.5 | 10 | >50 | ND |
| 280D11 | G1 | 1 | 1 | 0.9 | >40 | >50 | ND |
| 245E7 | G1 | 6 | 8 | 8 | 4 | >50 | >50 |
| 454C11 | G2a | 6 | >20 | 0.3 | 30 | ≧50 | ≧50 |
| 33F8 | G1 | 10 | ND | ND | ND | ND | ND |
| 369F10 | M | 10 | ND | ND | ND | ND | ND |
| 520C9 | G1 | >50 | >50 | 10 | >50 | | |
| 452F2 | G1 | 20 | | 10 | | | |
| 736G9 | G1 | >50 | >50 | 1.3 | >50 | | |
| 741F8 | G1 | >80 | >80 | | >80 | | |
| 758G5 | G1 | >50 | | 0.3 | | | |
| 761B10 | G1 | >50 | | 1.0 | | | |

ND = not determined.

In vivo Testing of Conjugates

1. Intact Antibody Conjugates

Conjugates of 245E7, 280D11, and 260F9 with RTA were made as above using iminothilane or SPDP as a coupling agent. The efficacies of these conjugates against MX-1 human breast tumor cells in vivo was evaluated as follows.

Female athymic Balb/c-nu/nu mice (20-24 g) were used. Fragments, 1.0 mm$^3$, were obtained from 600-800 mm$^3$ tumors with no signs of central necrosis and packed into a syringe. Mice were implanted s.c. with 0.05 ml of the suspension in the axillary region with mediolateral puncture. On day 7 or 14 after implant the mice were weighed and their tumor burdens were evaluated by measuring the implants with calipers. Mice were grouped accordingly to mean tumor size.

The conjugates were injected i.v. into the tail vein of control mice Q2D×6 to determine the maximum tolerable dose of the particular conjugate. Based on these results, dose regimens for administered the conjugates to tumor-bearing mice and control mice were selected. Groups of tumor-bearing mice and control mice were injected i.v. with the conjugates according to the chosen regimens. Animal reactions, side effects, and mortalities were monitored daily along with tumor volume and animal weight measurements. Changes in tumor volume at the end of the test period were calculated based on the average of the sum of measurements over the test period. The results of these tests are reported in Table 6 below.

2. Antibody Fragment Conjugates

Fab'$_2$ fragments or the monoclonal antibodies 520C9 and 280D11 were generated using techniques well known to those skilled int he art. They were conjugated and tested for in vivo efficacy in the MX-1human breast tumor cell model system as describe din section 1 above.

The 520C9 Fab'$_2$-IT-RTA conjugate was tested at concentrations of 25, 50, 100 and 200 μm/mouse. A single dose was delivered intravenously in 50 μl of sterile saline, and the effect of the conjugate on tumor volume monitored over a two week period. A significant decrease in tumor volume is observed at all concentrations tested for 520C9 Fab'$_2$-IT-RTA. At the end of 7 and 14 days the mean tumor volume for mice that received the 25 μg dose was about 200 m$^3$ and 850 m$^3$, whereas the mean tumor volume for control mice was about 350 m$^3$ and 1400 m$^3$, respectively. At 50 μg/mouse the mean tumor volume at 7 and 14 days was about 108 m$^3$ and 283 m$^3$, whereas for control mice the mean tumor volume was about 209 m$^3$ and 540 m$^3$, respectively. At 100 μg/mouse the mean tumor volume after 7 and 14 days was 79 m$^3$ and 188 m$^3$, whereas for control animals the mean tumor volume was 209 m$^3$and 540 m$^3$, respectively. Lastly, at 20 0μg/mouse the mean tumor volume after 7 and 14 days was about 100 m$^3$ and 325 m$^3$, whereas for control mice the mean tumor volume was about 325 m$^3$ and 1400 m$^3$, respectively.

For the 280D11 Fab'$_2$-IT-RTA conjugates, at a dose of 50 μg/mouse after and 14 days the mean tumor volume was about 101 m$^3$ and 230 m$^3$, whereas for control animals the mean tumor volume was about 140 m$^3$ and 580 m$^3$, respectively. The most marked difference was at the dose of 100 μg/mouse such that after 7 and 14 days the mean tumor volume was about 80 m$^3$ and 186 m$^3$, whereas for control animals the mean tumor volume was about 140 m$^3$ and 580 m$^3$.

TABLE 6

| Conjugate | LD$_{50}$(μg/m) | Dose/Schedule | Tumor Age/Volume (6-10 mice/gp) | % MX1-Tumor Growth Inhibitions | FBW/IBW |
|---|---|---|---|---|---|
| 245E7-SPDP-RTA | 410 | 125 μg iv/qod × 6 | 18d (300-400) | 74.8 (D14 only 3 animals | 1.15 |
| 245E7-IT-RTA | 350 | 200 μg iv/qod × 5 | 14d (100-200) | 62.5 (D14) p < 0.05 | 0.93 |
| 280D11-IT-RTA | 350 | 200 μg iv/qod × 5 | 14d (100-200 | 70.0 (D13) p < 0.01[1] | 0.99 |
|  |  | 200 μg iv/qod × 4 | 6d (25-50) | 80.0 (D14) p < 0.02 | 0.97 |
| 260F9-IT-RTA | 400 | 200 μg iv/qod × 5 | 14d (100-200) | 20.3 (D14 NS[2] | 1.02 |
|  |  | 100 μg/qod × 3-4 | 14d (100-200) | 17.6 (D14) NS[3] | 1.01 |
| 245E7-IT-RTA + 280D11-IT-RTA (cocktail) |  | 200 μg iv/qod × 5 | 14d (100-300) | 70.0 (D14) p < 0.01 | 1.00 |
|  |  |  |  | 80.0 (D10) p < 0.001 | 0.91 |

[1]Regression 60.5% (D6) p < 0.001 0.84
[2]50.8% (D11) p < 0.05 0.98
[3]44.8% (D11) p > 0.1 0.87
NS = not significant
D = days after initiation of treatment

Antibody Affinity and Antigen Density

Several of the claimed antibodies were iodinated and tested for binding to MCF-7 or BT-20 cells. The antibodies were labeled with $^{125}$I using chloramine T to a specific activity of approximately 10 μCi/μg. To determine immunoradiochemical purity, 100,000 cpm of two of the labeled antibodies in 0.5 ml fetal calf serum was serially absorbed with five aliquots of target cells for 15 minutes at 0° C. (generally 4,000,000 MCF-7 breast cancer cells per aliquot), and the remaining radioactivity in the supernatant after each absorption was determined.

For measurements of association constants, known concentrations of labeled and unlabeled monoclonal antibodies were incubated with target cells in fetal calf serum for 15 minutes in ice. Aliquots of the cell/antibody mix were then counted in a gamma counter or filtered through Microfold filter plates (V & P Scientific) and the filters counted. To account for unbound antibody retained in liquid on the filters, controls containing the same concentrations of antibody but no ells were done in parallel. Association constants and antigen copy number per target were calculated from the affinity test results and are reported in Table 7 below.

TABLE 7

| Antibody | n | Ka | nKa |
|---|---|---|---|
| 2G3 | 3.7e6 | 9.1e6 | 3.4e13 |
| 113F1 | 2.3e6 | 1.1e9 | 2.5e15 |
| 260F9 | 3.1e5 | 5.6e7 | 1.7e13 |
| 266B2 | 8.0e4 | 2.7e8 | 2.2e13 |
| 280D11 | 3.9e5 | 8.8e6 | 3.4e12 |
| 317G5 | 3.2e6 | 1.6e6 | 5.1e12 |
| 452F2 | 2.5e5 | 6.8e6 | 1.7e12 |
| 454C11 | 3.9e5 | 4.8e7 | 1.9e13 |
| 520C9 | 5.0e5 | 8.2e6 | 4.1e12 | n = the antigen copy number per MCF-7 cell;
Ka = association constant on MCF-7. nKa is the product of n and Ka and relates antibody concentration to antibody bound per cell.

Immunoprecipitation tests on the antibodies indicated that seven of them (454C11, 452F2, 520C9, 736G9, 741F8, 758G5, and 751B10) bind a common monomeric c.a. 210,000 dalton protein found in cancerous breast tissue. Six of the seven (452F2, 520C9, 736G9, 741F8, 758G5, and 761B10) are believed to recognize the same epitope on the 210,000 dalton protein. Of these six, relative affinity studies indicated that 520C9 had the highest association constant.

Samples of the hybridomas that produce the claimed monoclonal antibodies were deposited in the American Type Culture Collection (ATCC), 12301 Parklawn Drive, Rockville, Md. 20852-1776, USA. Only 520C9 was deposited on the six hybridomas that produce antibody that recognizes the same epitope on the 210,000 dalton protein. The five that were not deposited are considered to be functionally equivalent to 520C9. Their ATCC accession numbers and deposit dates for the deposited hybridomas are:

| Hybridoma/ Antibody Designation | Deposit Date | Accession No. |
|---|---|---|
| 260F9 | 1/27/84 | HB 8488 |
| 113F1 | 1/27/84 | HB 8490 |
| 2G3 | 1/27/84 | HB 8491 |
| 280D11 | 1/27/84 | HB 8487 |
| 266B2 | 1/27/84 | HB 8486 |
| 245E7 | 1/27/84 | HB 8489 |
| 454C11 | 1/27/84 | HB 8484 |
| 33F8 | | |
| 317G5 | 1/27/84 | HB 8485 |

| Hybridoma/ Antibody Designation | Deposit Date | Accession No. |
|---|---|---|
| 520C9 | | |
| 369F10 | 12/13/84 | HB 8682 |
| *260F9-1C9 | 11/7/84 | HB 8662 |

*This clone is a progeny of 260F9 and was found to be a better antibody producer than 260F9.

These deposits were made under Budapest Treaty and will be maintained and made accessible to others in accordance with the provisions thereof.

Modifications of the above-described modes for carrying out the invention and exemplified embodiments of the invention that are obvious to those of skill in the fields of hybridoma technology, immunology, and cancer diagnosis and therapy are intended to be within the scope of the following claims.

What is claimed is:

1. A monoclonal antibody that binds specifically to a monomeric 210 kD protein present in cancerous breast tissue.

2. A monoclonal antibody as described in claim 1, wherein said antibody is selected from the group consisting of 454C11 (ATTC No. HB8484), 452F2 (ATTC No. HB10811), 520C9 (ATTC No. HB8696), and 741F8 (ATTC No. HB10807).

3. A monoclonal antibody as described in claim 2, wherein said antibody has an association constant of about $4.8 \times 10^7$.

4. A monoclonal antibody as described in claim 2, wherein said antibody has an association constant of about $8.2 \times 10^6$.

* * * * *